United States Patent [19]

Wehner et al.

[11] 4,130,432
[45] Dec. 19, 1978

[54] TRIORGANOTIN CYANOMETALLATE COMPOUNDS

[75] Inventors: Hermann W. Wehner, Zwingenberg; Joachim Lorenz, Bensheim-Auerback, both of Germany

[73] Assignee: Ciba-Geigy Corporation, Ardsley, N.Y.

[21] Appl. No.: 751,229

[22] Filed: Dec. 16, 1976

[30] Foreign Application Priority Data

Dec. 23, 1975 [CH] Switzerland ............ 16699/75

[51] Int. Cl.² .......... C09D 5/14; C09D 5/16; C09D 5/18
[52] U.S. Cl. ............... 106/15 R; 44/68; 71/97; 106/288Q; 252/49.7; 252/431 N; 260/45.75 K; 260/429.7; 546/12
[58] Field of Search .......... 260/429.7, 429.5, 270 PY; 424/288; 106/15 AF, 15 R

[56] References Cited

U.S. PATENT DOCUMENTS

| 3,070,433 | 12/1962 | Schlör et al. ............ 424/288 X |
| 3,683,089 | 8/1972 | Deinet ............ 424/288 |
| 3,848,336 | 3/1976 | Stutz ............ 424/288 X |

OTHER PUBLICATIONS

Spivak, Dissertation Abstracts Int. B. 31 (8) pp. 4563–4564 (1971).
Chemical Abstracts 77 20754x (1972).
Chemical Abstracts 78 84537b (1973).
Rochow et al., JACS 75 3099–3101 (1953).
Paller, The Chemistry of Organotin Compounds, Academic Press, pp. 274–277 (1971).
Cotton Progress in Inorganic Chem., 7 322–332 (1966).
Stone et al, Adv. in Organometallic Chem. 7 222–224 (1968).

Newmann, The Organic Chemistry of Tin, Intersc. Publ. N.Y., 242–243 (1971).

Primary Examiner—Helen M. S. Sneed
Attorney, Agent, or Firm—Luther A. R. Hall

[57] ABSTRACT

Compounds of the general formula I

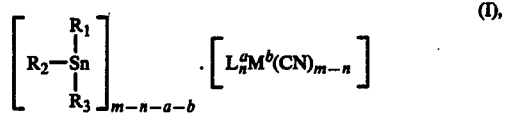

wherein
m is 4, 6 or 8,
n is 0 or 1,
a is 0 or 1,
b is 1, 2, 3, 4 or 5,
each of
$R_1$, $R_2$ and $R_3$ independently represents an alkyl group, an alkyl group which is substituted or which contains —CO— or —C(=O)—O— in the chain, an alkenyl, cycloalkyl, alkylcycloalkyl group, a substituted or unsubstituted aryl group or a substituted or unsubstituted aralkyl group,
L represents $NH_3$, pyridine, water, CO, NO or a halogen atom, and
M if m is 4, represents Ni(O), Ni(I), Ni(II), Pd(II), Pt(II), Cu(I), Cu(II), Ag(I), Au(III), Zn(II),Cd(II), Hg(II), and if m is 6 represents Ti(III), V(II), V(III), Cr(I), Cr(II), Cr(III), Mn(I), Mn(II), Mn(III), Te(I), Re(I), Re(II), Re(III), Re(IV), Fe(II), Fe(III), Ru(II), Ru(III), Os(II), Co(I), Co(II), Co(III), Rh(III), Ir(III), Pt(IV), and if m is 8, represents Ti(III), Mo(IV), Mo(I), W(IV), W(V), Mn(IV) or (Re(V), as biocides.

10 Claims, No Drawings

TRIORGANOTIN CYANOMETALLATE COMPOUNDS

The present invention relates to novel triorgano-tin cyanometallate compounds, a process for their manufacture, the use of these novel compounds as biocides and compositions which contain them as active substance.

Triorgano-tin compounds are known biocides. Accordingly, different triorgano-tin derivatives have been used in a variety of fields of pest control. Their use against weeds and fungi is known for example from DAS No. 1,055,871, against animal pests, such as mice and rats, for example from French patent specification No. 1,400,314, against growth on underwater constructions from British patent specification 1,001,369, and against fungi and bacteria for example from German patent specification No. 950,970. In addition, their use as stabilisers in plastics, such as polyvinyl chloride, has also been described for example in U.S. Pat. No. 2,977,379.

However, considerable difficulties are encountered when using such triorgano-tin compounds as total biocides. The biocidal activity spectrum is not only heavily dependent on their structure, but is restricted in addition by the solubility and diffusion properties of the triorgano-tin compounds employed.

In order to broaden the activity spectrum, attempts have been made to combine different organo-tin biocides. It is known to combine the components by simple physical mixing or also by intramolecular linkage. Both variants have many disadvantages which derive chiefly from the differences in the solubility and diffusion properties of the components, as a consequence of which in turn the desired broad activity spectrum is not attained. Thus, for example, it is known from K. Yoshikawa, Kogyo Kagaku Zasshi 67 (5), 740 (1964) [C.A. 61, 11032] that precisely such biocidal mixtures very often fail to bring about the desired effect. For example, the (1:1) mixture of $(n-C_4H_9)_3SnCl$ and $[(n-C_4H_9)_3Sn]_2O$ exhibited a certain synergism, whereas the (1:1) mixture consisting of $(n-C_4H_5)SnCl$ and $(n-C_4H_9)_2(CH)_3SnOAc$ showed evidence of a marked antagonism.

A novel class of triorgano-tin compounds has now been found, which possess very good biocidal properties in a surprisingly broad sphere of application. The compounds are characterised by exceptionally low solubility, yet on the other hand they possess good compatibility with and can be readily distributed in most conventional carriers. The advantages accruing from this low solubility compared with many known triorgano-tin compounds are described hereinafter.

The compounds of the present invention have the general formula I

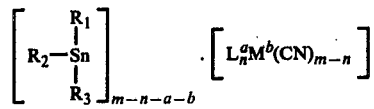

wherein
m is 4, 6 or 8,
n is 0 or 1;
a is 0 or 1,
b is 1, 2, 3, 4, or 5,
each of $R_1$, $R_2$ and $R_3$ independently represents an alkyl group, an alkyl group which is substituted or which contains —CO— or —C(=O)—O— in the chain, an alkenyl, cycloalkyl, alkylcycloalkyl group, a substituted or unsubstituted aryl group or a substituted or unsubstituted aralkyl group, L represents $NH_3$, pyridine, water, CO, NO or a halogen atom, and M if m is 4, represents Ni(O), Ni(I), Ni(II), Pd(II), Pt(II), Cu(I), Cu(II), Ag(I), Au(III), Zn(II), Cd(II), Hg(II), and if m is 6, represents Ti(III), V(II), V(III), Cr(I), Cr(II), Cr(III), Mn(I), Mn(II), Mn(III), Tc(I), Re(I), Re(II), Re(III), Re(IV), Fe(II), Fe(III), Ru(II), Ru(III), Os(II), Co(I), Co(II), Co(III), Rh(III), Ir(III), Pt(IV), and if m is 8, represents Ti(III), Mo(IV), Mo(V), W(IV), W(V), Mn(IV) or Re(V).

The symbols in the formula I can have the following meanings:

m is the coordination number of the central atom employed. For the transition metals it is 4, 6 or 8, depending on the metal. The coordination numbers for a wide variety of cyano complexes are to be inferred for example from the article by B. M. Chadwick and A. G. Sharpe in Adv. in Inorg. Chem. and Radiochem., 8, 83 (1966).

n is the number of foreign ligands in the complex. It is known that, in cyanometals, one or more cyano molecules can be replaced by other ligands. This circumstance is described in condensed form in the above mentioned Chadwick article. However, only compounds in which n is 0 or 1 are of practical importance for the present invention. Preferably, n is 0.

a is the charge of the foreign ligands and is mostly 0. However, if L is NO, then a is frequently +1; but complexes in which a must be accorded the value $-1$ (for example in $K_3[Cr(III)(CN)_5NO]$ are also known.

b is the charge of the central atom. Preferably the charge is +1, +2, or +3.

An alkyl group represented by each of $R_1$, $R_2$ and $R_3$ independently is for example an alkyl group of 1 to 18 carbon atoms, such as a methyl, ethyl, propyl, n-butyl, n-pentyl, n-hexyl, n-heptyl, n-octyl, n-decyl, n-dodecyl, n-tetradecyl, n-hexadecyl or n-octadecyl group, and is most preferably an alkyl group of 1 to 8 carbon atoms, in particular a methyl, ethyl, n-butyl or n-octyl group.

An alkenyl group represented by each of $R_1$, $R_2$ and $R_3$ independently is for example an alkenyl group of 2 to 18 carbon atoms, such as a vinyl, allyl, 1-butenyl, 2-butenyl, 2-pentenyl, 2-hexenyl, 2-octenyl, 2-decenyl, 2-dodecenyl or 2-octadecenyl group, and is most preferably a vinyl or allyl group. A cycloalkyl group represented by each of $R_1$, $R_2$ and $R_3$ independently is for example a cycloalkyl group of 5 to 12 carbon atoms, such as a cyclopentyl, cyclohexyl or cyclooctyl group, and is preferably a cyclohexyl group. An alkylcycloalkyl group represented by each of $R_1$, $R_2$ and $R_3$ independently is for example an alkylcycloalkyl group of 6 to 18 carbon atoms, such as an α-methylcyclopentyl, α-methylcyclohexyl, β-ethylcyclohexyl or tert.-octylcyclohexyl group.

An aryl group represented by each of $R_1$, $R_2$ and $R_3$ independently is for example an aryl group of 6 to 16 carbon atoms, such as phenyl, α- or β-naphthyl group, preferably a phenyl group.

A substituted aryl group represented by each of $R_1$, $R_2$ and $R_3$ independently is for example an aryl group of 6 to 16 carbon atoms which is substituted by alkyl, alkoxy, alkylthio or oxoalkyl or carbalkoxyalkyl, each of 1 to 12 carbon atoms, or which is substituted by 1 to 2 halogen atoms, in particular chlorine atoms or by a nitro group, and is for example, a tolyl, 2,4-xylyl, 2,6-xylyl, p-chlorophenyl, 3-chloro-p-tolyl, p-tert.-butylphenyl, 2,3-dichlorophenyl, p-n-octylphenyl, p-n-dodecylphenyl, o-nitrophenyl, o-ethoxyphenyl, or ethylthiophenyl or 3-oxo-heptanyl or carboethoxypropyl group.

An aralkyl group represented by each of $R_1$, $R_2$ and $R_3$ independently is for example an aralkyl group of 7 to 17 carbon atoms, such as a benzyl, α-phenylethyl or 2-phenylpropyl group, and is preferably a benzyl group.

A substituted aralkyl group represented by each of $R_1$, $R_2$ and $R_3$ independently is for example an aralkyl group which is substituted by alkyl of 1 to 12 carbon atoms or by 1 to 2 halogen atoms, in particular chlorine atoms, or by a nitro group, and is for example an α-dimethylbenzyl group.

X represents CN or SCN. It is known that SCN is able to be bonded both through the sulphur and through the nitrogen atom.

L denotes the foreign ligand. The most important examples are: NO, $H_2O$, CO and $NH_3$, of which NO is preferred.

M is the symbol for the central atom and can represent any transition metal which occurs in cyano complexes. It is most surprising that strongly reducing metals are also suitable as M for the compounds of the formula I, since the IV-valent state of tin in these compounds is extremely stabilized. Metal centres are preferred which have a coordination number of 4, such as Ni(II), Cu(I) or Zn(II), in particular Ni(II), and also those with a coordination number of 6, such as Ti(III), Mn(II), Fe(II), Fe(III), Co(III), in particular Fe(II), Fe(III), Mn(II) and Co(III).

Preferred compounds are those of the formula I, wherein
  m is 4 or 6,
  b is 1, 2 or 3,
  each of
    $R_1$, $R_2$ and $R_3$ independently represents an alkyl group of 1 to 18 carbon atoms, an alkenyl group of 2 to 18 carbon atoms, a cyclohexyl group of 5 to 12 carbon atoms, an alkylcycloalkyl group of 6 to 18 carbon atoms, or an aryl group which is unsubstituted or substituted by alkyl, alkoxy or alkylthio or oxoalkyl or carbalkoxyalkyl, each of 1 to 12 carbon atoms, or by 1 to 2 halogen atoms or by a nitro group, or an aralkyl group of 7 to 17 carbon atoms which is unsubstituted or substituted by alkyl of 1 to 12 carbon atoms or by 1 to 2 halogen atoms or by a nitro group,
and the symbols n, a, L and M, if m is 4 or 6, are as defined hereinbefore, and in particular those of the formula I, wherein
  m is 4 or 6,
  b is 1, 2 or 3,
  each of
    $R_1$, $R_2$ and $R_3$ independently represents an alkyl group of 1 to 8 carbon atoms, a cyclohexyl, phenyl, benzyl, vinyl or allyl group, and
  M if m is 4, represents Ni(II), Cu(I) or Zn(II), and, if m is 6, represents Ti(III), Mn(II), Fe(II), Fe(III), Co(II) or Co(III).

The particularly preferred compounds of the formula I also include those wherein
  m is 4 or 6,
  b is 1, 2 or 3, and
  M if m is 4, represents Ni(II), and, if m is 6, represents Fe(II), Fe(III) or Co(III) or Mn(II).

Mention is to be made of those preferred compounds in which each of $R_1$, $R_2$ and $R_3$ represents an alkyl group of 1 to 8 carbon atoms, a cyclohexyl, phenyl, benzyl, vinyl or allyl group, and in particular those in which $R_1$ and $R_2$ are methyl or n-butyl groups and $R_3$ is a methyl, n-butyl, n-octyl or phenyl group. Preferably two, but most preferably all three, of the radicals $R_1$, $R_2$ and $R_3$ are identical. The sum of the carbon atoms in the radicals $R_1$, $R_2$ and $R_3$ is preferably 3 to 24 and especially 3 to 18.

Examples of compounds of the formula I are:

tetra-[tri-butyl-tin]-hexacyanomanganate (II)
tris-[tri-butyl-tin]-hexacyanoferrate (III)
bis-[tri-butyl-tin]-mono-nitrosyl-pentacyanoferrate (II)
bis-[tri-butyl-tin]-tetracyanonickelate (II)
tetra-[dimethyl-phenyl-tin]-hexacyanoferrate (II)
tris-[tri-methyl-tin]-hexacyanoferrate (III)
bis-[dimethyl-phenyl-tin]-mono-nitrosyl-pentacyanoferrate (II)
bis-[dimethyl-phenyl-tin]-tetracyanonickelate (II)
bio-[tri-benzyl-tin]-mono-nitroxyl-pentacyanoferrate (II)
tetra-[dimethyl-octyl-tin]-hexacyanocobaltate (II)
tris-[trivinyl-tin]-monoaquo-pentacyanocobaltate (II)
tetra-[tri-(o-ethoxyphenyl)-tin]-hexacyanomanganate (II)
bis-[diamyl-methyl-tin]-monoaquocyanocobaltate (III)
tris-[di-methyl-phenyl-tin]-hexacyanocobaltate (III)
bis-[methyl-butyl-octyl-tin]-tetracyanonickelate (II)
tris-[tri-butyl-tin]-tetracyanocuprate (I)
tris-[di-butyl-ethyl-tin]-tetracyanocuprate (I)
bis-[tri-allyl-tin]-tetracyanocuprate (II)
bis-[tri-butyl-tin]-tetracyanozincate (II)
bis-[tri-amyl-tin]-tetracyanozincate (II)
bis-[tri-butyl-tin]-tetracyanomercurate (II)
tris-[trimethyl-tin]-hexacyanoferrate (III)
tris[tripropyl-tin]-hexacyanoferrate (III)
tris-[tricyclohexyl-tin]-hexacyanoferrate (III)
tris-[dimethyl-octyl-tin]-hexacyanoferrate (III)
tris-[diethyl-octyl-tin]-hexacyanoferrate (III)
tris-[dimethyl-butyl-tin]-hexacyanoferrate (III)
tris-[diethyl-butyl-tin]-hexacyanoferrate (III)
tris-[dibutyl-methyl-tin]-hexacyanoferrate (III)
tris-[dibutyl-ethyl-tin]-hexacyanoferrate (III)
tris-[triphenyl-tin]-hexacyanoferrate (III)
tris-[trivinyl-tin]-hexacyanoferrate (III)
tris-[tricyclohexyl-tin]-hexacyanoferrate (III)
tris-[tri-neopentyl-tin]-hexacyanoferrate (III)
bis-[trimethyl-tin]-tetracyanonickelate (II)
bis-[tripropyl-tin]-tetracyanonickelate (II)
bis-[trineophyl-tin]-tetracyanonickelate (II)
bis-[dimethyl-octyl-tin]-tetracyanonickelate (II)
bis-[diethyl-octyl-tin]-tetracyanonickelate (II)
bis-[dimethyl-butyl-tin]-tetracyanonickelate (II)
bis-[diethyl-butyl-tin]-tetracyanonickelate (II)
bis-[dibutyl-methyl-tin]-tetracyanonickelate (II)
bis-[dibutyl-ethyl-tin]-tetracyanonickelate (II)
bis-[triphenyl-tin]-tetracyanonickelate (II)
bis-[trivinyl-tin]-tetracyanonickelate (II)
bis-[tri-cyclohexyl-tin]-tetracyanonickelate (II)
bis-[tri-neopentyl-tin]-tetracyanonickelate (II)

bis-[trimethyl-tin]-mono-nitrosyl-pentacyanoferrate (II)
bis-[tripropyl-tin]-mono-nitrosyl-pentacyanoferrate (II)
bis-[triamyl-tin]-mono-nitrosyl-pentacyanoferrate (II)
bis-[dimethyl-octyl-tin]-mono-nitrosyl-pentacyanoferrate (II)
bis-[diethyl-octyl-tin]-mono-nitrosyl-pentacyanoferrate (II)
bis-[dimethyl-butyl-tin]-mono-nitrosyl-pentacyanoferrate (II)
bis-[diethyl-butyl-tin]-mono-nitrosyl-pentacyanoferrate (II)
bis-[dibutyl-methyl-tin]-mono-nitrosyl-pentacyanoferrate (II)
bis-[dibutyl-ethyl-tin]-mono-nitrosyl-pentacyanoferrate (II)
bis-[triphenyl-tin]-mono-nitrosyl-pentacyanoferrate (II)
bis-[trivinyl-tin]-mono-nitrosyl-pentacyanoferrate (II)
bis-[tri-cyclohexyl-tin]-mono-nitrosyl-pentacyanoferrate (II)
bis-[tri-neophyl-tin]-mono-nitrosyl-pentacyanoferrate (II).

The compounds are obtained advantageously by reacting the corresponding triorgano-tin halide of the formula II

wherein $R_1$, $R_2$ and $R_3$ are as defined in formula I and Q represents a reactive group, such as a halogen atom, in particular a chlorine or bromine atom, or an acyloxy group, such as an acetyloxy group, or an OH or $O_{\frac{1}{2}}$ group, with an ammonium or alkali metal cyanometallate of the formula III

wherein L, M, a, b m and n are as defined in formula I and A represents $NH_2$, Li, Na or K, preferably Na or K, especially K. The compounds of the formula II are known. The compounds of the formula III are also known and can be prepared by methods which are summarised by Chadwick and Sharpe, Adv. in Inorg. Chem. and Radiochem., 8, 83 (1966). The triorgano-tin compounds of the formula II and the ammonium or alkali metal metallate are most advantageously used in a molar ratio of approx. (m-n-a-b):1. The reaction can be carried out at room temperature and the triorgano-tin compound is dissolved in any inert organic solvent which is miscible with water.

Suitable solvents are, for example, alcohols containing 1 to 4 carbon atoms; amides, such as dimethyl formamide; sulphoxides, such as dimethyl sulphoxide, ethers, such as dioxane. The use of alcohols, such as methanol or ethanol, is preferred. The ammonium or alkali metal cyano- or thiocyano-metallate is preferably dissolved in water or in a mixture consisting of water and a water-miscible organic solvent. Suitable organic solvents are those referred to above. The ratio of water to organic solvent is determined basically by the solubility of the metallate employed and in practice is usually 1:1. In a preferred modification of the process, a solution of the alkali metal cyano metallate in water is charged into the reaction vessel and a solution of the triorgano-tin halide in methanol is added thereto.

On account of its low solubility, the desired product precipitates rapidly and in high purity from most of these solvent mixtures. Only a few strongly polar aprotic organic solvents, such as dimethyl formamide or hexamethylphosphoric triamide, are able to dissolve some of the novel triorgano-tin cyanomethallates. It is then expedient to add an excess of water when the reaction is complete. The addition of water also has the advantage in the other process modifications that excess triorgano-tin compounds of the formula II — if these are water-soluble — are dissolved out.

It is known that the solutions or suspensions of a number of the complexes of the formula III are sensitive to oxidation, in particular those compounds in which the central atom can be oxidised by oxygen to a higher valency. In these cases it is necessary to carry out the above described process in an inert gas atmosphere.

The majority of the compounds of the present invention are pigment-like and are characterised by low solubility both in water and in almost all organic solvents, so that they are obtained in the reaction medium in good yield and purity. This low solubility is of great technical usefulness, since as a consequence the compounds are exceptionally suitable for long-term protection. Whereas many known biocides possess good activity properties, they do not ensure long-term protection, since the compounds are rapidly extracted by organic solvents or water from the material to be protected. The fact that they have good compatibility with and can be readily distributed in a wide variety of carrier materials increases the outstanding biocidal action of the compounds of the present invention.

The compounds of the present invention provide a broad activity spectrum for the control of animal and plant pests, thus resulting in a wide range of application possibilities, for example as bactericides, disinfectants, as agents for combating the formation of mucus in paper manufacture, as fungicides, insecticides, acaricides, or herbicides, such as algicides. Furthermore, the novel compounds are highly suitable for use as industrial antimicrobial agents for protecting material, for example wood, pulp and paper, textiles and leather, dyes, varnishes, antifouling paints and similar coating materials, optical and other kinds of glass, cooling water, plastics, rubber and adhesives, cutting oils, petroleums, lubricants, waxes and fuels and other materials. Interestingly, the compounds of the invention are suitable in addition for use as catalysts for polymerisation reactions.

Depending on the purpose for which they are used, the compounds are employed in the concentrations known to the skilled person. The limits of the customary concentrations are provided by the following values: whilst in cooling water concentrations in the ppm range suffice, concentrations of up to 40% by weight are usual in antifouling recipes.

The compounds can be applied in pure form or together with carriers as dusts, tracking agents or mists. They can also be suspended in liquid coating agents, in which case wetting agents and emulsifiers can assist the even distribution of the active compound to form homogeneous dispersions. Further biocides, such as insecticides, can also be added.

A preferred field of application is that of protective coatings, in particular antifouling paints, on an organic basis, which contain 0.5 to 40% by weight, preferably 3 to 15% by weight, referred to the total mixture, of a compound of the formula I or mixtures thereof, in addition to the conventional base materials and additives.

Conventional base materials for antifouling paints are the raw materials for paints and varnishes which are known to the skilled person and designated as binders, such as natural and synthetic resins, homo- and copolymeric products with the monomers vinyl chloride, vinylidene chloride, styrene, vinyl toluene, vinyl esters, acrylic acid and methacrylic acid and esters thereof, as well as chlorinated rubber, natural and synthetic rubber (optionally chlorinated or cyclised), reactive resins, such as epoxide resins, polyurethane resins, unsaturated polyesters which can optionally be converted into film-forming products of higher molecular weight by adding hardeners.

The binders can be liquid or in the form of solutions. If dissolved binders, and also thermoplastics, are used, a protective film can also be formed by evaporating the solvent. Solid coating compounds can be applied to objects for example in the powder coating process. Further customary base materials are for example tar, modifiers, dyes, inorganic or organic pigments, fillers and hardeners.

Finally, the compounds of the present invention can also be used in elastomeric coatings.

The invention is illustrated in more detail by the following non-limitative Examples. Parts and percentages are by weight.

EXAMPLE 1

Tetra-[tributyl-tin]-hexacyanoferrate (II)

42.2 g (0.1 mole) of potassium hexacyanoferrate (II)-trihydrate are dissolved in a 1:1 mixture of water and methanol. In an inert gas atmosphere and with vigorous stirring, a solution of 130.4 g (0.4 mole) of tributyl tin chloride in methanol is added dropwise. The reaction mixture is allowed to stand for 2 hours and then additionally diluted with water. The precipitated needles are filtered off and washed with water/methanol and finally with ether. The light green pigment-like tetra-[tributyl tin]-hexacyanoferrate(II) is not fusible up to 340° C. and the elemental analysis yields the following values (in %).

|  | C | H | Fe | N | Sn |
|---|---|---|---|---|---|
| Calculated | 47.3 | 7.9 | 4.1 | 6.1 | 34.6 |
| Found | 47.3 | 7.7 | 4.1 | 6.1 | 34.4 |

EXAMPLE 2

Tri-[tributyl tin]-hexacyanoferrate (III)

An aqueous solution containing 32.9 g (0.1 mole) of potassium hexacyanoferrate (III) is charged into a reaction vessel and a solution of 97.6 g (0.3 mole) of tributyl-benzchloride is added dropwise. After diluting the reaction mixture with water, the orange- to reddish-coloured precipitate is filtered off and washed with methanol and thereafter with ether. The yield of tri-[tributyl tin]-hexacyanoferrate (III) is 94%. Product A is not fusible up to 340° C. and the elemental analysis yields the following values (in %):

|  | N | Fe |
|---|---|---|
| Calculated | 7.8 | 5.2 |
| Found | 7.4 | 4.9 |

The product undergoes *exothermic* conversion at 216° C. into a steel-blue modification (product B). If A is dried at 160° C., a mixed form is obtained (see application examples). The products A, B and mixed form possess different biological activity. Product B is sparingly soluble in hot hexamethylphosphoric triamide; product A is insoluble in cold dimethyl formamide, but readily soluble in hot hexamethylphosphoric triamide (emerald green).

The toxicity of A is $LD_{50}$ (oral administration to rats), 3100 mg/kg.

Irritation (rabbits' eyes) slight.
Irritation (rabbit skin) moderate.

The product undergoes *endothermic* conversion at 156° C. into a dark violet modification (product C). If product D (Example 3) is dried at 140° C., a mixed form is obtained (see application examples). D, C and mixed form possess different biological activity.

D is readily soluble in cold dimethyl formamide and in cold hexamethylphosphoric triamide (almost colourless).

C is very sparingly soluble in hot hexamethylphosphoric triamide (emerald green).

EXAMPLE 3

Di-[tributyl tin]-mononitrosyl-pentacyanoferrate (II)

A solution of 65.1 g (0.2 mole) of tributyl tin chloride in methanol is charged into a reaction vessel and a solution of 36.9 g (0.1 mole) of potassium mononitrosyl-pentacyanoferrate (II) in methanol is added dropwise. For the rest, the procedure as described in Example 2 is carried out. The yield is 92%. The flesh-coloured product D is not fusible up to 340° C. The elemental analysis yields the following values (in %):

|  | C | H | Fe | N | Sn |
|---|---|---|---|---|---|
| Calculated | 43.8 | 6.8 | 7.0 | 10.6 | 29.8 |
| Found | 43.7 | 6.9 | 6.0 | 10.0 | 30.0 |

EXAMPLE 4

Di-[tributyl tin]-tetracyanonickelate (II)

The process of Example 2 is repeated, except that 65.1 g (0.2 mole) of tributyl tin chloride are reacted with 26.9 g (0.1 mole) of potassium tetracyanonickelate. The yield is 99%. The product is not fusible up to 340° C. and its elemental analysis yields the following values (in %):

|  | C | H | N | Ni | Sn |
|---|---|---|---|---|---|
| Calculated | 45.3 | 7.3 | 7.5 | 7.9 | 32.0 |
| Found | 45.0 | 7.0 | 7.6 | 7.9 | 32.0 |

The product is moderately soluble in dimethyl formamide.

EXAMPLE 5

Tetra-[dimethylphenyl tin]-hexacyanoferrate (II)

The process of Example 2 is repeated, except that 104.4 g (0.4 mole) of dimethylphenyl tin chloride in methanol are reacted with 42.2 g (0.1 mole) of potassium hexacyanoferrate (II) in water. The yield of tetra-[dimethylphenyl tin]-hexacyanoferrate is 84%. The product has a melting point of 75°-77° C. and the elemental analysis yields the following values (in %):

|  | C | H | Fe | N | Sn |
|---|---|---|---|---|---|
| Calculated | 40.9 | 4.0 | 5.0 | 7.5 | 42.6 |
| Found | 41.1 | 4.0 | 4.6 | 7.0 | 42.1 |

The product is moderately soluble in hot dimethyl formamide.

EXAMPLE 6

Tri-[dimethylphenyl tin]-hexacyanoferrate (III)

The process of Example 2 is repeated, except that 78.3 g (0.3 mole) of dimethylphenyl tin chloride in ethanol are reacted with 32.9 g of potassium hexacyanoferrate (III) in water. The yield of tri-[dimethylphenyl tin]-hexacyanoferrate is 95%. The ocre-coloured product E is not fusible up to 340° C. and the elemental analysis yields the following results (in %):

|  | Fe | N |
|---|---|---|
| Calculated | 6.3 | 9.4 |
| Found | 5.8 | 9.0 |

The product undergoes *exothermic* conversion at 194° C. into a light violet modification (product F). Both products possess different biological activity. Product E is sparingly soluble in cold dimethyl formamide, moderately soluble in hot hexamethylphosphoric triamide. Product F is very sparingly soluble in hot hexamethylphosphoric triamide. Both products possess different biological activity.

EXAMPLE 7

Di-[dimethylphenyl tin]-mononitrosyl-pentacyanoferrate (II)

The process of Example 2 is repeated, except that 52.2 g (0.2 mole) of dimethylphenyl tin chloride in methanol are reacted with 36.9 g (0.1 mole) of potassium mononitrosylpentacyanoferrate (II) in water. The brownish substance, di-[dimethylphenyl tin]-mononitrosyl-pentacyanoferrate (II), is not fusible up to 340° C. and has a tin content of 35% (theory: 35.6%). The substance is readily soluble in dimethyl formamide.

EXAMPLE 8

Di-[dimethylphenyl tin]-tetracyano-nickelate (II)

The process of Example 2 is repeated, except that 56.9 g (0.2 mole) of dimethylphenyl tin acetate are reacted with 26.9 g (0.1 mole) of potassium tetracyanonickelate. The yield of di-[dimethylphenyl tin]-tetracyanonickelate (II) is 82%. The product has a melting point of 265° C. and the elemental analysis yields the following values (in %):

|  | Ni | Sn |
|---|---|---|
| Calculated | 9.6 | 38.7 |
| Found | 9.2 | 38.4 |

The substance is moderately soluble in dimethyl formamide.

EXAMPLE 9

Tri-[tributyl tin]-hexacyanocobaltate (III)

Synthesis as in Example 2.
Substances employed: 10 g (0.03 mole) of potassium hexacyanocobaltate (III) in water, 29.3 g (0.09 mole) of tributyl tin chloride in methanol.

The colourless product is obtained in 85% yield (m.p. 300° C.). Product G, $D_{16}$-1271, undergoes *endothermic* conversion at 131° C. into a second and also colourless modification (product H). Both modifications possess different biological activity.

Product G is sparingly soluble in hot dimethyl formamide, but is readily soluble in cold hexamethylenephosphoric triamide. Product H is readily soluble in hot hexamethylenephosphoric triamide.

EXAMPLE 10

Tetra-[tributyl tin]-hexacyanomanganate (II)

Synthesis as in Example 2 but in an inert gas atmosphere.

Substances employed: 8.8 g (0.02 mole) of potassium hexacyanomanganate (II) in water. 26.04 g (0.08 mole) of tributyl tin chloride in methanol.

The light brown product is obtained in 78% yield (m.p. 300° C.). The substance is sparingly soluble in hot dimethyl formamide and moderately soluble in hot hexamethylenephosphoric triamide.

The following substances are prepared by the process of Example 2 starting from the potassium cyanomethallate and triorgano-tin chlorides.

| Substance | Colour | Yield |
|---|---|---|
| $[(CH_3)_3Sn]_4 Co^{II}(CN)_6$ | colourless | 94% |
|  | violet | 32% |
| $[(O_2N-\bigcirc-CH_2)_3Sn]_3 Ti^{III}(CN)_6$ |  |  |
| $[(\bigcirc H)_3Sn]_2 Zn^{II}(CN)_4$ | colourless | 58% |
| $[(C_3H_7)_3Sn]_3 Cu^{I}(CN)_4$ | colourless | 61% |

EXAMPLE 11

The broad microbial activity of the compounds of the present invention was ascertained by determining the minimum inhibitory concentrations by means of the gradient test. The following microorganisms were used for the test:

(1) *Staph. aureus* SG 511
(2) *Str. faecalis* ATCC 10 541
(3) *Bac. subtilis* ATCC 6633
(4) *Escherichia coli* NCTC 8196
(5) *Proteus vulgaris* ATCC 9484
(6) *Salm. thyphimurium* K 1127
(7) *Pseudomonas aeruginosa* ATCC 10 145
(8) *Candida albicans* ATCC 10 259
(9) *Asp. elegans* M 3637

The results reported in the table (inhibitory concentrations in ppm) are obtained for example with the following compounds of the invention:

(A) di-[dimethylphenyl tin]-tetracyanonickelate (II),
(B) di-[tributyl tin]-tetracyanonickelate (II),
(C) di-[tributyl tin]-mononitrosyl-pentacyanoferrate (II), mixture of annealed and unannealed form — see compound examples, (D) tri-[tributyl tin]-hexacyanoferrate (III), mixture of annealed and unannealed form — see compound examples.

| Com- | Microorganism | | | | | | | | |
|---|---|---|---|---|---|---|---|---|---|
| pound | 1 | 2 | 3 | 4 | 5 | 6 | 7 | 8 | 9 |
| A | 30 | 90 | 30 | 13 | 30 | 8 | 30 | 30 | 15 |
| B | 3 | 3 | 1 | 5 | 5 | 30 | 220 | 3 | 3 |
| C | 6 | 7 | 1 | 9 | 30 | 30 | 30 | 3 | 3 |
| D | 7 | 7 | 3 | 15 | >300 | >300 | >300 | 3 | 3 |

EXAMPLE 12

The following compounds of the invention are tested in three different antifouling paints I, II and III:

tri-[tributyl tin]-hexacyanoferrate (III), mixture of annealed and unannealed form — see compound examples di-[tributyl tin]-tetracyanonickelate (II)

di-[tributyl tin]-mononitrosyl-pentacyanoferrate (II), mixture of annealed and unannealed form — see compound examples tetra-[tributyl tin]-hexacyanoferrate (II).

The first paint (I) is a chlorinated rubber antifouling paint which contains the compound to be tested as sole antifouling additive in a concentration of 28.5 percent by volume of the total solid. In the second antifouling paint (II), based on vinyl chloride copolymer/colophonium as binder, the compound to be tested is used jointly with copper(I) oxide, each in an amount of 14.25 percent by volume. In the third antifouling paint, on the basis of vinyl chloride copolymer as binder, 21.4 percent by volume of the compound to be tested is used jointly with 7.1 percent by volume of zinc oxide. The composition of the antifouling paints is as follows:

| (I) | parts by weight |
|---|---|
| chlorinated rubber type 10 | 71 |
| plasticiser (CLOPHEN A 60) | 6 |
| epoxidised soya oil | 2 |
| talc | 32 |
| iron oxide red | 55 |
| barytes | 50 |
| aromatic white spirit | 115 |
| butyl acetate | 7 |
| xylene | 115 |

The above mentioned compounds were used singly in the following amounts:

| | |
|---|---|
| $[(n-C_4H_9)_3Sn]_3[Fe(CN)_6]$ | 42 |
| $[(n-C_4H_9)_3Sn]_2[Ni(CN)_4]$ | 41 |
| $[(n-C_4H_9)_3Sn]_2[Fe(CN)_5NO]$ | 42 |
| $[(n-C_4H_9)_3Sn]_4[Fe(CN)_6]$ | 41 |

| (II) | parts by weight |
|---|---|
| vinyl chloride-acetate resin (91% of VC, 3% of VAC, 6% of VA) | 41 |
| colophonium | 14 |
| tris-tolyl-phosphate | 7 |
| epoxidised soya oil | 2 |
| talc | 32 |
| iron oxide red | 55 |
| barytes | 50 |
| methyl isobutyl ketone | 79 |
| xylene | 83 |
| $Cu_2O$ | 99 |

| | |
|---|---|
| $[(n-C_4H_9)_3Sn]_3[Fe(CN)_6]$ | 21 |
| $[(n-C_4H_9)_3Sn]_2[Ni(CN)_4]$ | 21 |
| $[(n-C_4H_9)_3Sn]_2[Fe(CN)_5NO]$ | 21 |
| $[(n-C_4H_9)_3Sn]_4[Fe(CN)_6]$ | 21 |

| III | parts by weight |
|---|---|
| vinyl chloride-acetate resin (86% of VC, 14% of VAC) | 59 |
| tris-tolyl-phosphate | 4 |
| epoxidised soya oil | 4 |
| talc | 32 |
| iron oxide red | 55 |
| barytes | 50 |
| methyl isobutyl ketone | 111 |
| aromatic white spirit | 44 |
| xylene | 108 |
| ZnO | 49 |

| | |
|---|---|
| $[(n-C_3H_9)_3Sn]_3[Fe(CN)_6]$ | 32 |
| $[(n-C_4H_9)_3Sn]_2[Ni(CN)_4]$ | 31 |
| $[(n-C_4H_9)_3Sn]_2[Fe(CN)_5NO]$ | 32 |
| $[(n-C_4H_9)_3Sn]_4[Fe(CN)_6]$ | 32 |

The antifouling paints I, II and III are applied to prepared test plates in a thickness of approx. 60μ (plate preparation: steel plates, sandblasted, vinyl butyral primer, protective coating of red lead against corrosion, one red lead coating on the basis of chlorinated rubber being prepared for the chlorinated rubber antifouling paint, and one on the basis of a vinyl chloride copolymer for the other two paints).

The test was carried out under conditions of actual practice by putting down the test plates (a) in a subsidiary branch of the Rhine with heavy algae growth, (b) in a test station in the North Sea (Cuxhaven) where heavy animal growth, especially of balanidae, occurs.

Evaluation

The evaluation is made according to a rating in which 0 denotes complete growth and 10 complete freedom from growth. The rating figures from 1 to 9 correspond then to a gradation in the intensitiy of growth. For practical purpose, a rating of 7 to 10 suffices for an antifouling paint used for protection against algae, whilst one of 9 to 10 is required for protection against the growth of animal organisms.

(a) Algae

The behaviour of the test plates was observed over a period of 8 weeks. Test plates which had been coated with a normal paint, i.e. one containing no antifouling additive, had a rating of 1 to 2 after only 2 weeks.

(b) Balanidae

Testing took place during the growth period from the beginning of June to the beginning of November. Paints containing no antifouling additive were completely overgrown (rating 0) under the conditions prevailing in the test station after only 4 weeks.

The followng results were obtained:

| Compound | Algae I | Algae II | Algae III | Balanidae I | Balanidae II | Balanidae III |
|---|---|---|---|---|---|---|
| $[n\text{-}(C_4H_9)_3Sn]_3[Fe(CN)_6]$ | 10 | 8 | 9 | 10 | 1 | 10 |
| $[n\text{-}(C_4H_9)_3Sn]_2[Ni(CN)_4]$ | 9 | 10 | 9 | 10 | 10 | 10 |
| $[n\text{-}(C_4H_9)_3Sn]_2[Fe(CN)_5NO]$ | 7 | 8 | 9 | 9 | 5 | 10 |
| $[n\text{-}(C_4H_9)_3Sn]_4[Fe(CN)_6]$ | 9 | 9 | 8 | 10 | 0 | 10 |

We claim:

1. A compound of the general formula I

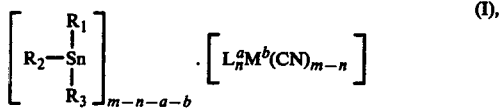

(I)

wherein m is 4, 6 or 8 n is 0 or 1, a is 0 or 1, b is 1, 2, 3, 4 or 5, each of $R_1$, $R_2$ and $R_3$ independently represents an alkyl group of 1 to 18 carbon atoms, an alkenyl group of 2 to 18 carbon atoms, a cycloalkyl group of 5 to 12 carbon atoms, an alkylcycloalkyl group of 6 to 18 carbon atoms, or an aryl group of 6 to 16 carbon atoms which is unsubstituted or substituted by alkyl, alkoxy or alkylthio or oxoalkyl or carbalkoxyalkyl, each of 1 to 12 carbon atoms, or by 1 to 2 halogen atoms or by a nitro group, or an aralkyl group of 7 to 17 carbon atoms which is unsubstituted or substituted by alkyl of 1 to 12 carbon atoms or by 1 to 2 halogen atoms or by a nitro group, L represents $NH_3$, pyridine, water, CO, NO or a halogen atom, and M if m is 4, represents Ni($\overline{O}$), Ni(I), Ni(II), Pd(II), Pt(II), Cu(I), Cu(II), Ag(I), Au(III), Zn(II), Cd(II), Hg(II), and if m is 6 represents Ti(III), V(II), V(III), Cr(I), Cr(II), Cr(III), Mn(I), Mn(II), MN(III), Te(I), Re(I), Re(II), Re(III), Re(IV), Fe(II), Fe(III), Ru(II), Ru(III), Os(II), Co(I), Co(II), Co(III), Rh(III), Ir(III), Pt(IV), and if m is 8, represents Ti(III), Mo(IV), Mo(I), W(IV), W(V), Mn(IV) or Re(V), and with the proviso that $R_1$, $R_2$ and $R_3$ may not all be methyl or all be phenyl at the same time when M is Fe(II) or Fe(III).

2. An antifouling paint composition containing 0.5 to 40% by weight of the composition of a biocidal compound, or mixture of said compounds, of the general formula I

(I)

wherein m is 4, 6 or 8, n is 0 or 1, a is 0 or 1, b is 1, 2, 3, 4 or 5, each of $R_1$, $R_2$ and $R_3$ independently represents an alkyl group of 1 to 18 carbon atoms, an alkenyl group of 2 to 18 carbon atoms, a cycloalkyl group of 5 to 12 carbon atoms, an alkylcycloalkyl group of 6 to 18 carbon atoms, or an aryl group of 6 to 16 carbon atoms which is unsubstituted or substituted by alkyl, alkoxy or alkylthio or oxoalkyl or carbalkoxyalkyl, each of 1 to 12 carbon atoms, or by 1 to 2 halogen atoms or by a nitro group, or an aralkyl group of 7 to 17 carbon atoms which is unsubstituted or substituted by alkyl of 1 to 12 carbon atoms or by 1 to 2 halogen atoms or by a nitro group, L represents $NH_3$, pyridine, water, CO, NO or a halogen atom, and M if m is 4, represents Ni($\overline{O}$), Ni(I), Ni(II), Pd(II), Pt(II), Cu(I), Cu(II), Ag(I), Au(III), Zn(II), Cd(II), Hg(II), and if m is 6 represents Ti(III), V(II), V(III), Cr(I), Cr(II), Cr(III), Mn(I), Mn(II), Mn(III), Te(I), Re(I), Re(II), Re(III), Re(IV), Fe(II), Fe(III), Ru(II), Ru(III), Os(II), Co(I), Co(II), Co(III), Rh(III), Ir(III), Pt(IV), and if m is 8, represents Ti(III), Mo(IV), Mo(I), W(IV), W(V), Mn(IV) or (Re(V).

3. A composition according to claim 2 containing 3 to 15% by weight of the composition of a biocidal compound, or mixture of said compounds, of general formula I.

4. A compound of the formula I according to claim 1, wherein m is 4 or 6, and b is 1, 2 or 3.

5. A compound of the formula I according to claim 1, wherein each of $R_1$, $R_2$ and $R_3$ independently represents an alkyl group of 1 to 8 carbon atoms, a cyclohexyl, phenyl, benzyl, vinyl, neopentyl, neophyl or allyl group.

6. A compound of the formula I according to claim 1, wherein m is 4 or 6, b is 1, 2 or 3, each of $R_1$, $R_2$ and $R_3$ independently represents an alkyl group of 1 to 8 carbon atoms, a cyclohexyl, phenyl, benzyl, vinyl or allyl group, and M if m is 4, represents Ni(II), Cu(I) or Zn(II) and, if m is 6, represents Ti(III), Mn(II), Fe(II), Fe(III), Co(II) or Co(III).

7. A compound of the formula I according to claim 1, wherein m is 4 or 6, b is 1, 2 or 3, and M if m is 4, represents Ni(II), and if m is 6, represents Fe(II), Fe(III), Co(II) or Co(III).

8. A compound of the formula I according to claim 1, wherein $R_1$ and $R_2$ represents methyl or n-butyl groups and $R_3$ represents a methyl, n-butyl, n-octyl or phenyl group.

9. A compound of the formula I according to claim 1, wherein n is 0.

10. A compound of the formula I according to claim 1, wherein L is NO.

* * * * *